United States Patent [19]

Yamamoto et al.

[11] Patent Number: 4,929,081
[45] Date of Patent: May 29, 1990

[54] SYSTEM FOR DETECTING DEFECTS IN A REGULARLY ARRANGED PATTERN SUCH AS AN INTEGRATED CIRCUIT OR THE LIKE

[75] Inventors: Yoko Yamamoto; Hitoshi Tanaka; Noboru Mikami, all of Hyogo, Japan

[73] Assignee: Mitsubishi Denki Kabushiki Kaisha, Tokyo, Japan

[21] Appl. No.: 423,551

[22] Filed: Oct. 13, 1989

Related U.S. Application Data

[63] Continuation of Ser. No. 161,089, Feb. 26, 1988, abandoned.

[30] Foreign Application Priority Data

Feb. 27, 1987 [JP] Japan .................................. 62-45631

[51] Int. Cl.$^5$ .............................................. G01B 9/02
[52] U.S. Cl. ..................................... 356/354; 356/347; 350/364
[58] Field of Search ....................... 356/347, 354, 237; 350/3.64, 3.58

[56] References Cited

U.S. PATENT DOCUMENTS

| | | |
|---|---|---|
| 4,330,205 | 5/1982 | Murakami et al. |
| 4,330,775 | 5/1982 | Iwamoto et al. |
| 4,360,269 | 11/1982 | Iwamoto et al. |
| 4,448,527 | 5/1984 | Milana .................. 356/237 |
| 4,674,824 | 6/1987 | Goodman et al. .................. 350/3.64 |

OTHER PUBLICATIONS

Journal of Photographic Science; vol. 34, 1986, pp. 1–10 "Inspection of Integrated Photomasks Using Optical Data Processing Techniques"-Watson et al.
Lyman, Electronics, Mar. 5, 1987, pp. 75–76 "Moving Wafer Inspection Into the Fast Lane".
Optical Engineering, Sep./Oct. 1985, vol. 24, No. 5, pp. 731–734 "Holographic Optical Processing for Submicrometer Defect Detection"-Fusek et al.

Primary Examiner—Vincent P. McGraw
Assistant Examiner—S. A. Turner
Attorney, Agent, or Firm—Bernard, Rothwell & Brown

[57] ABSTRACT

A pattern defect detecting system for an integrated semiconductor circuit or the like, utilizing the phenomenon that in the case of a test pattern having regularity, the intensity of diffracted light appearing on a back-focal plane of a lens is high, while defects or foreign matters not having regularity are low in the intensity of diffracted light. As a concrete example, an optical space modulator is used to record only an intense light portion in real time. The recorded diffraction pattern can be erased easily by, for example, application of voltage and radiation of light. A spatial filter can be prepared in real time in 1:1 correspondence to a test sample. Besides, even in the case of change of test pattern, an immediate action can be taken for continuous detection of defects, thus permitting test on-line.

8 Claims, 5 Drawing Sheets

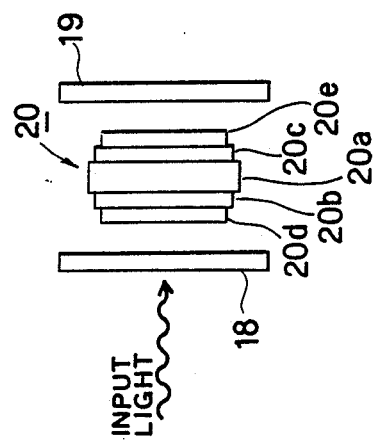
FIG. 3
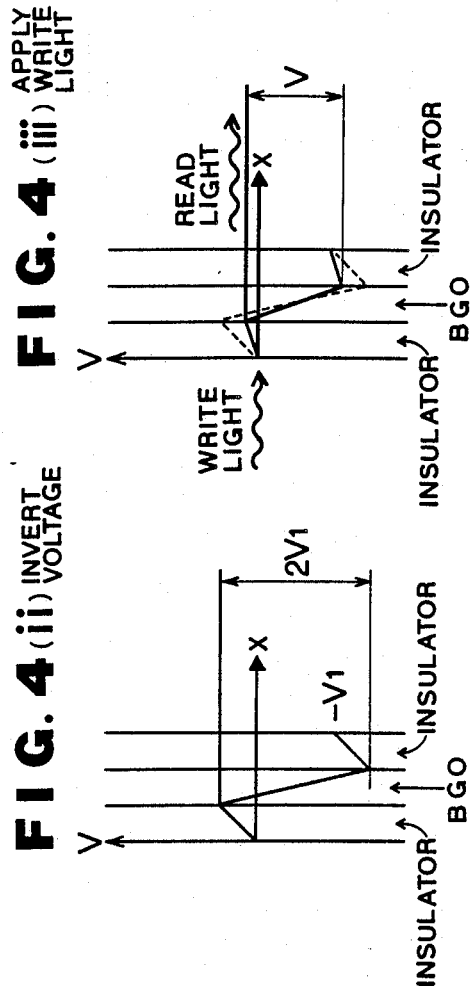

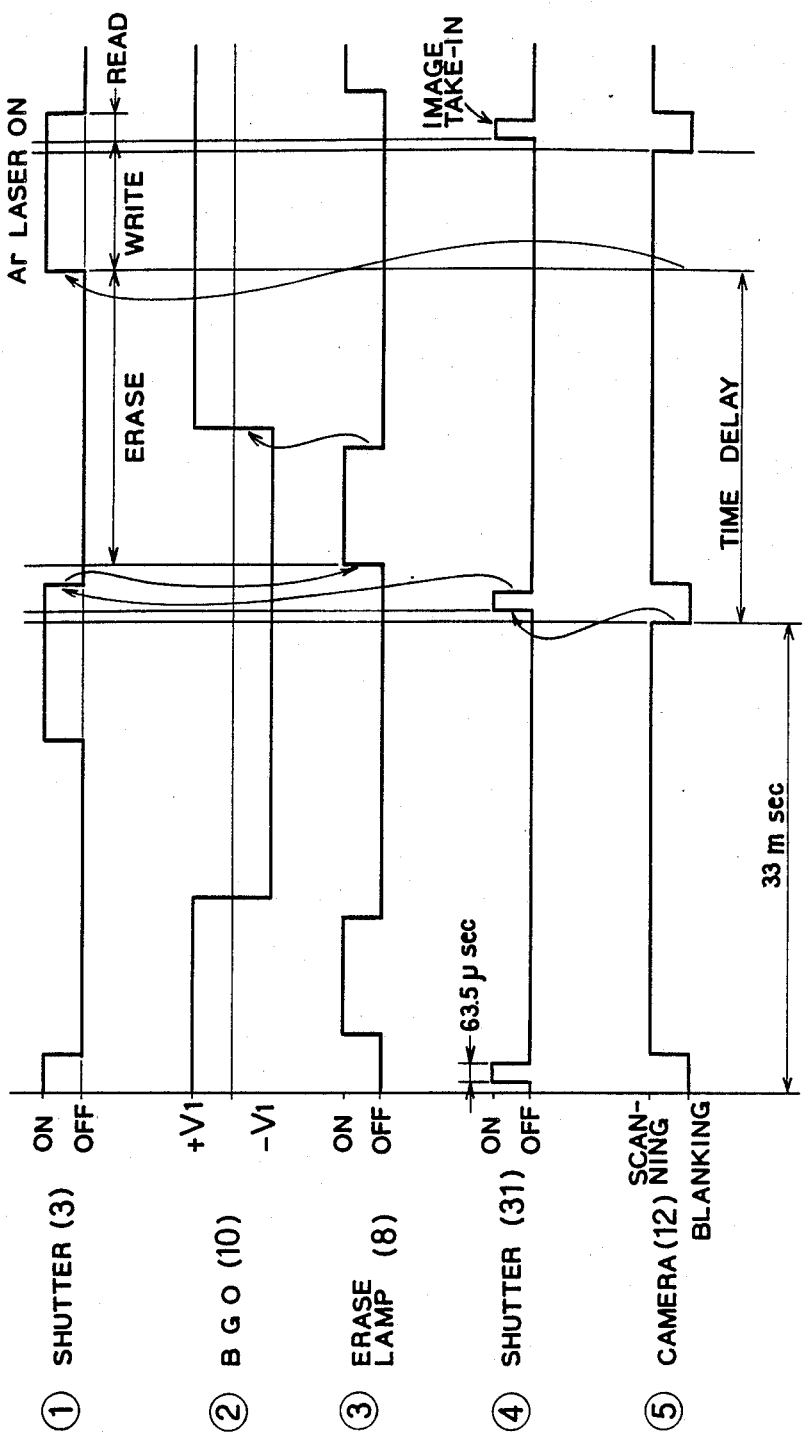

SYSTEM FOR DETECTING DEFECTS IN A REGULARLY ARRANGED PATTERN SUCH AS AN INTEGRATED CIRCUIT OR THE LIKE

This is a continuation of application Ser. No. 161,089 filed Feb. 26, 1988, and now abandoned.

BACKGROUND OF THE INVENTION

1. Field of the Invention

The present invention relates to a pattern defect detecting system and more particularly to a pattern defect detecting system which detects defects or foreign matters on the surface of a regularly arranged test pattern such as an integrated semiconductor circuit which has been subjected to patterning, using an optical space modulator capable of recording and erasing diffracted light of a test sample in real-time operations as spatially filtering means.

2. Prior Art

Heretofore, as a pattern defect detecting system of this type there has been known, for example, the one disclosed in Japanese Patent Publication No. 16542/81, in which there is made inspection of pattern using a transmitted image of a test sample.

On the other hand, as a like system using a reflected image of a test sample there has been proposed by the same applicant the system described in the specification of Japanese Patent application No. 38770/87.

FIG. 1 is a block diagram illustrating such a conventional reflection type pattern defect detecting system as referred to above. In FIG. 1, the reference numeral 1 denotes a coherent light source such as a laser; the numeral 2 denotes a collimator for enlarging the light emitted from the light source 1 into collimated light; numerals 5 and 32 each denote a half mirror; and numeral 4 denotes a test sample placed on a stage, the test article having a regularly arranged test pattern. Further, numeral 6 denotes an X-Y stage for moving the test sample 4 and numeral 7 denotes a convex lens for condensing the light reflected from the test sample 4. Numeral 12 denotes a defect detecting camera disposed in the position where the test sample 4 is imaged by the lens 7; numeral 13 denotes a signal processing section for processing an output signal provided from the camera 12, to detect a defective position; and numeral 14 denotes a monitor television connected to the signal processing section 13 to display the defect. Further, numeral 17 denotes a spatial filter disposed in a backfocal position of the lens 7 to cut off diffracted light based on a normal pattern of the test sample 4. Numeral 33 denotes a camera for detecting the position of a diffraction pattern based on reflected light in the post-focal position of the lens 7, and numeral 34 denotes a control unit which calculates the amount of dislocation from a normal position of the diffraction pattern and provides a correction command to tilt angle adjusting mechanisms 35, 36 and a rotational angle adjusting mechanism 37.

The operation of the above conventional system will now be described.

The light emitted from the coherent light source 1 is reflected by the half mirror 5 and then directed to the test pattern of the test sample 4. The reflected light from the test sample 4 passes through the half mirror 5 and condensed by the lens 7, then split into two light beams. One beam reaches the spatial filter 17, while the other is incident on the diffraction pattern position detecting camera 33. The spatial filter 17 exposes in that position the diffraction pattern of the normal pattern onto a photographic plate and after development processing it is returned exactly to the exposure position and fixed there. Next, during detection of a pattern defect, the diffracted light of the reflected light is observed by the camera 33 to detect the position of the diffraction pattern. The control unit 34 provides a command for correcting the deviation in tilt angle and that in rotational angle of the test sample 4 from the optical axis, to the adjusting mechanisms 35, 36 and the rotary stage 37. Then, registration is made between the diffraction pattern of the filter 17 and the diffracted light of the normal pattern of the test sample 4. As a result, the diffracted light of the normal pattern during the detection is removed by the diffraction pattern on the filter, a defect signal is observed by the camera 12, and the pattern defect is displayed on the monitor 14.

Thus, in the conventional pattern defect detecting system, when the tilt angle and rotational angle of the test sample vary with respect to the optical axis, there occurs deviation between the position of the diffraction pattern which appears on the post-focal plane of the lens and that of the diffraction pattern recorded on the filter. Consequently, every time the test sample is moved, there are detected deviations of tilt angle and rotational angle, so it is necessary to correct the above positions. This is inconvenient. Further, since the filter material is the photographic plate, a new filter must be prepared at every change in pattern of the test sample, thus requiring development processing in an off-line.

SUMMARY OF THE INVENTION

It is a primary object of the present invention to provide a useful pattern defect detecting system free from the drawbacks of the above conventional system.

It is another object of the present invention to provide a pattern defect detecting system in which, at every detection of a pattern defect of say an integrated semiconductor circuit, a spatial filter which is in 1:1 correspondence to the test sample can be prepared in off-line and that in real time.

It is a further object of the present invention to provide a pattern defect detecting system not requiring correction of the tilt angle and rotational angle of a test sample and so permitting the use of an optical system of an extremely simple structure in attaining a high-speed defect detecting processing of high performance.

Other and further objects of the present invention will become apparent from the following description of an embodiment taken in connection with the accompanying drawings.

BRIEF DESCRIPTION OF THE DRAWINGS

FIG. 3 is an explanatory view showing a construction of a spatial filter;

FIG. 4 (*i–iii*) is a graph for explaining the operation of the spatial filter;

FIG. 5 is a time chart for explaining the operation of the system illustrated in FIG. 2;

PREFERRED EMBODIMENT OF THE INVENTION

A pattern defect detecting system according to an embodiment of the present invention will be described hereinunder using the accompanying drawings.

Figure 1:
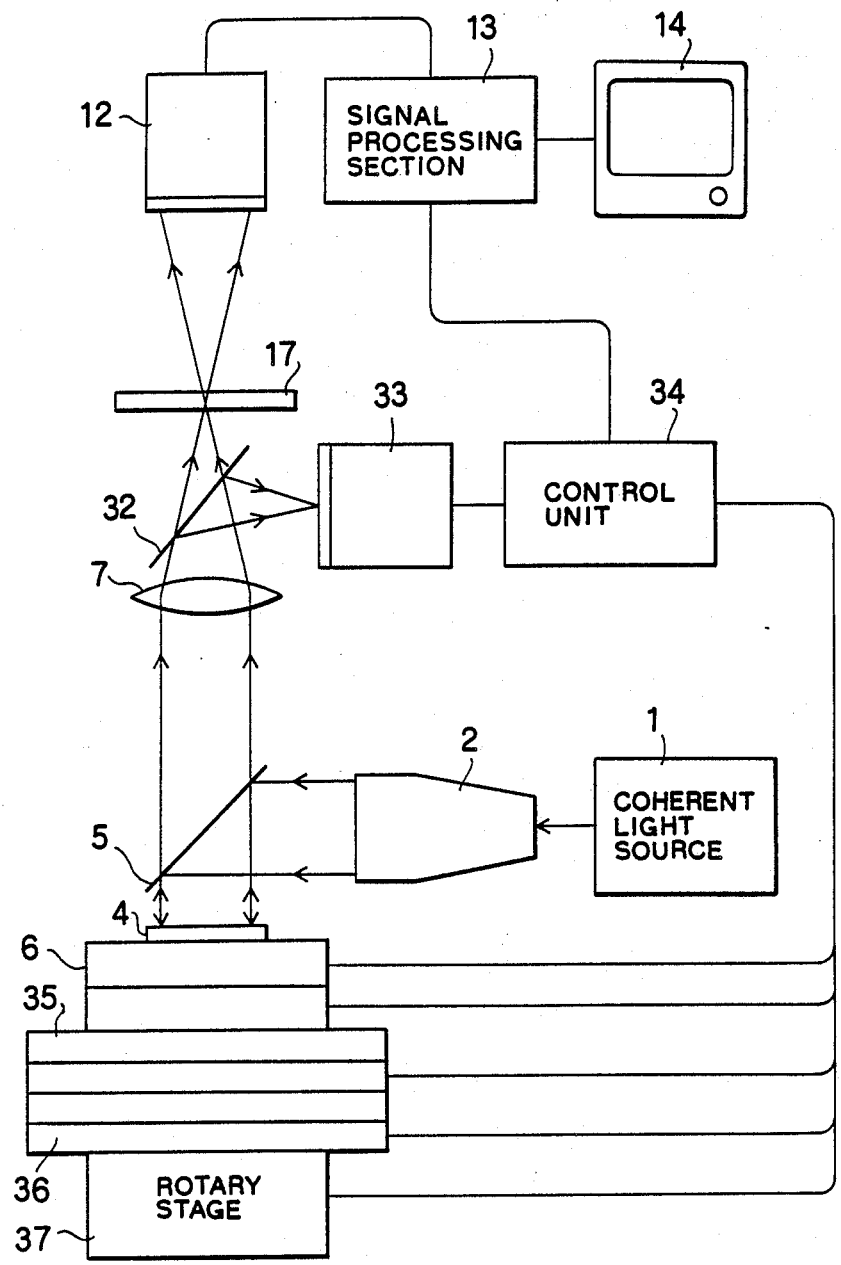
FIG. 1 is a block diagram of a conventional pattern defect detecting system.
Figure 2:
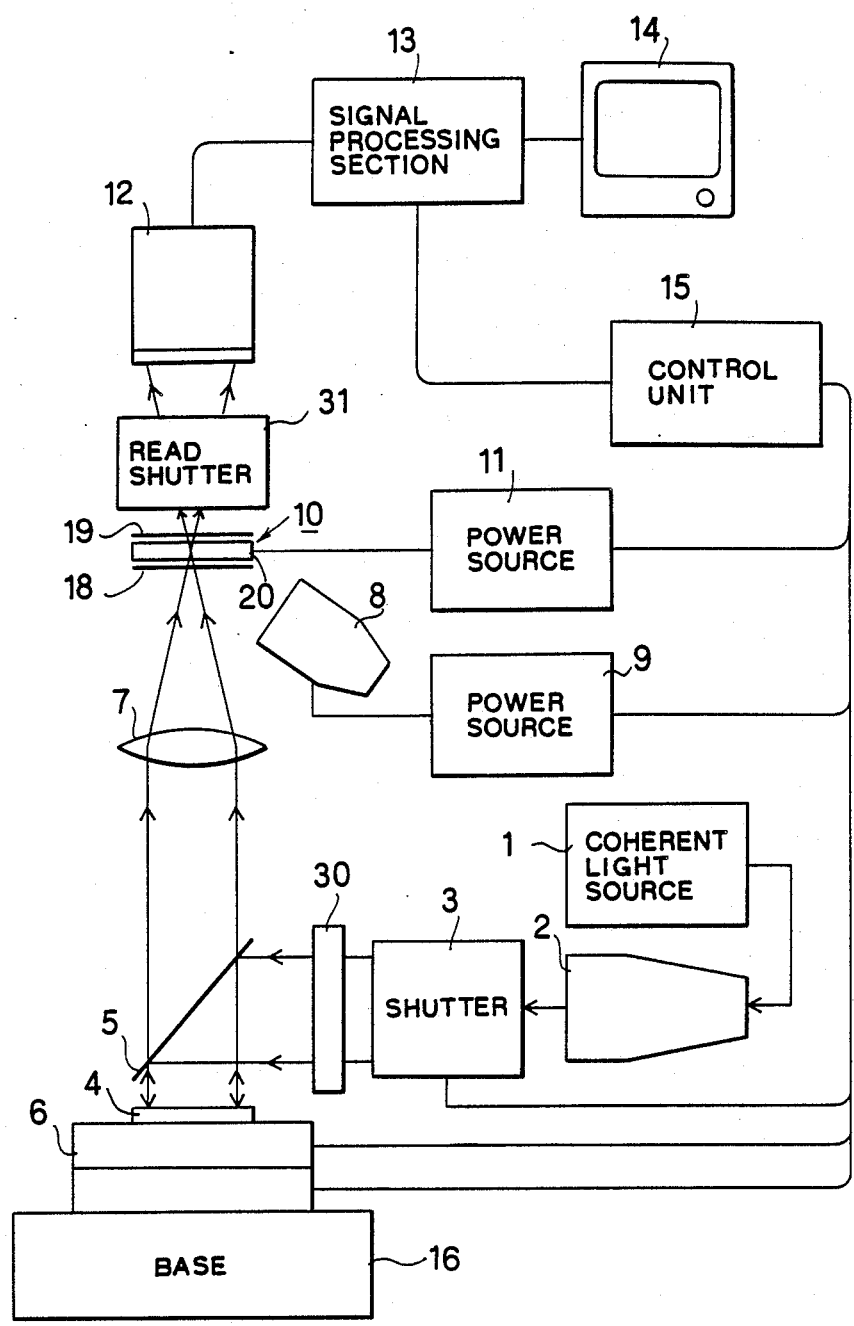
FIG. 2 is a block diagram of a pattern defect detecting system according to an embodiment of the present invention.

Referring first to FIG. 2, the system is illustrated in the form of a block diagram, in which the same portions as in FIG. 1 are indicated by the same reference numerals. Explanation on those common portions will be omitted. In FIG. 2, the numeral 3 denotes a shutter; numeral 8 denotes a white light lamp for initializing an optical space modulator 10; numeral 9 denotes a power source section of the lamp; and numeral 11 denotes a power source section of the optical space modulator 10. Further, numeral 15 denotes a control unit for controlling the shutter 3, power sources 9, 11, an X-Y stage 6 and a signal processing section 13. Numerals 16, 30 and 31 denote a base, a polarizer and a read shutter, respectively.

The optical space modulator 10 functions to record diffracted light of a normal pattern of a test sample in real time and cut off diffracted light of a defective pattern. The modulator 10 also functions to erase the recorded diffraction pattern in real time.

For example, the modulator 10 is composed of an electro-optical material (PROM element) 20 having photoconductivity and Pockels effect such as BSO ($Bi_{12}SiO_{20}$) [see "Optronics" No. 11 (1984), p. 59] or BGO [see "Kogaku" Vol. 14, No. 1 (1985), p. 19], a polarizer 18 and an analyzer 19.

For example, the following description is now provided about cut-off characteristics of a spatial filter constituted using BGO as the electro-optical material.

In constituting this spatial filter, insulating films 20b and 20c are formed on both sides of BGO 20a as shown in FIG. 3, then clear electrodes 20d and 20e are attached to the outsides of the insulating films 20b and 20c, respectively, and two polarizing plates 18 and 19 are disposed orthogonally to each other. Of the two, the polarizing plate 18 positioned on an input side of light and the other 19 on an output side of light will be hereinafter referred to as a polarizer and an analyzer, respectively.

The phase rotation induced by the electrooptical effect (Pockels effect) of the BGO 20a in such spatial filter is proportional to the voltage developed across the BGO 20a. When the polarizer 18 and the analyzer 19 are disposed orthogonally to each other, and if the voltage developed across the BGO 20a is V, the amplitude A of the output light through the BGO 20a is:

$$A = A_0 \sin\left(\frac{\pi}{2} \cdot \frac{V}{V_h}\right)$$

wherein $V_h$ represents a voltage developed across the BGO 20a when the phase rotation is 90°, which voltage is proportional to the wave length and is 5.6 kV at λ=633 mm, $V_h$ being constant for the thickness of the device.

The operation of the spatial filter will now be explained. Although the operation of the BGO is classified into erase cycle, write cycle and read cycle, explanation will be made in a divided manner into two which are erase cycle and write/read cycle.

(1) Erase Cycle

As shown in FIG. 4(i), a voltage of $V_1$ to $V_h/2$ is applied across the BGO and erase light is directed to the BGO. The voltage difference across the BGO becomes zero due to the photoconductivity of the BGO, so there does not occur phase rotation of light and input light beams are all cut off. Then, as shown in FIG. 4(ii), the erase light is extinguished and the above applied voltage is inverted. In this state, a voltage of $2V_1$ to $V_h$ is applied across the BGO, the phase rotation of light becomes about 90°, and the BGO transmits most of the light.

(2) Write/Read Cycle

As shown in FIG. 4(iii), upon radiation of write light, the voltage across the BGO drops gradually due to the photoconductivity of the BGO and the amount of phase rotation of light decreases, so that the amount of transmitted light becomes smaller. And the stronger the light applied to the BGO, the larger the amount of light cut off.

The operation of the device using the BGO will be explained below with reference to the waveform diagram of FIG. 5.

When linearly polarized Ar laser light is applied through the half mirror to the test sample 4 placed on the X-Y table 6 which moves at a constant speed, the test sample 4 having a regular pattern, the reflected light thereof is condensed by the lens 7 and there is obtained a diffraction pattern on the BGO 20 which is placed in the focal position, while in the photographing position of the camera 12 there is obtained an imaged pattern. In this arrangement, ① the shutter 3, ② BGO 20, ③ erase lamp 8, ④ shutter 31 and ⑤ camera 12 are operated at the timing shown in FIG. 5. As a result, it becomes possible to process the image of only defective pattern free from regular pattern by means of a processor. The following is an explanation on the timing chart of FIG. 5.

Start-up trigger is made using a vertical synchronizing signal of the camera 12 which serves as a detector. Consequently, one cycle becomes 1/30 second and classification is made into the three steps of erase, write and read. These steps will be explained below one by one.

(a) Erase Step

Upon closure of the read shutter 31, the shutter 3 is closed to cut off laser light and the erase lamp 8 is turned on. After applying a sufficiently erasing quantity of light to the test pattern, the erase lamp 8 is turned off. After confirmation of this, the voltage of the BGO 20 is inverted, waiting for the start of write.

(b) Write Step

Upon lapse of a certain time after the issuance of the vertical synchronizing signal of the camera 12, the shutter 3 is opened to radiate laser beam for the start of write. Delay time is calculated on the basis of the time required for providing laser light in a quantity necessary to prepare a spatial filter.

(c) Read Step

During the vertical synchronizing period of the camera 12 (the period during which the camera does not read out a signal), the shutter 31 is opened for only 63.5 μsec and a defect signal is printed on the photographing plane of the camera. The release time of the shutter 31 was determined from the condition that a moving image may move by only one pixel (picture element) on the image plane.

Figure 6:
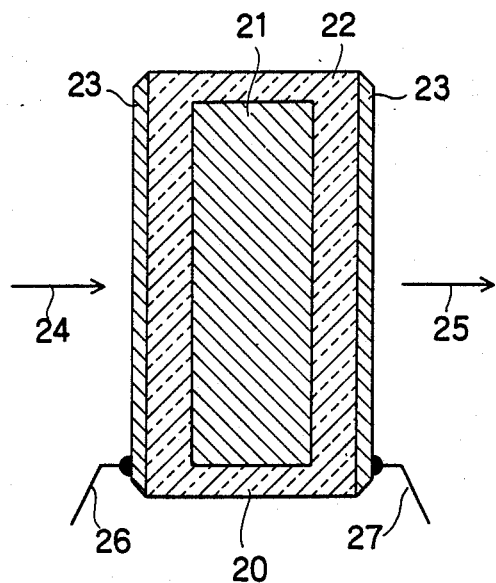
FIG. 6 is a longitudinal sectional view showing a construction of an electronic optical device used in the pattern defect detecting system embodying the invention.

FIG. 6 is a sectional view showing the construction of an electro-optical device 20 which is used in the pattern defect detecting system embodying the invention. In FIG. 6, the reference numerals 21, 22, 23, 24 and 25 denote a single crystal plate, an insulator, a clear electrode, an input light and an output light, respectively, and numerals 26 and 27 each denote a lead electrode.

The operation of this electro-optical device will be explained below with reference also to FIG. 2.

Figure 7:
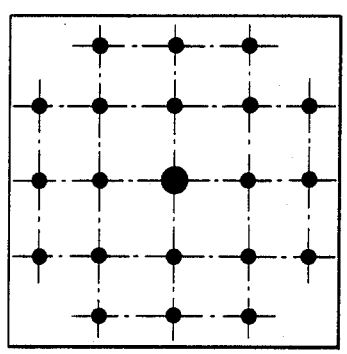
FIG. 7 is an explanatory view showing a diffraction pattern based on diffracted light of a normal pattern.

Light having a wave length of 488 nm emitted from the argon laser device 1 serving as a coherent light source is enlarged by the collimator 2, reflected by the half mirror 5 and applied to the semiconductor wafer 4. The reflected light from the wafer 4 passes through the half mirror 5 and is condensed by the lens 7, then reaches the filter portion constituted by the optical space modulator 10. The light which has passed through the polarizer 18 reaches the electro-optical device 20, whereupon only intense light is recorded by virtue of photoconductivity to change the birefringence based on the Pockels effect. In this case, if the normal pattern of the test sample has a repeating structure, such a diffraction pattern as shown in FIG. 7 appears on the plane of the optical space modulator 10 which is placed in the back-focal position of the lens. Thus, the optical space modulator 10 records only diffracted light having a high intensity distribution and changes birefringence. On the other hand, diffracted light of a pattern not having a repeating structure such as the defect signal is weak, so it is scarcely recorded and there occurs no change in birefringence. That is, the intense diffracted light from a normal pattern and the weak diffracted light from a defect pass through portions different in birefringence so the outgoing light beams are different in their polarized conditions. In this connection, if a polarizing plate which intercepts the polarization of the diffracted light of the normal pattern is disposed as the analyzer 19 on the output side of the device, diffracted light from a defect will be incident on the camera 12 and detected as a defect signal.

Thus, the detection of a defect signal can be done by only providing an extremely short time difference with respect to the spatial filter which has recorded the diffraction pattern of the normal pattern. For testing the next test sample, the laser light is once again cut off with the shutter 3 and then the white light lamp 8 is turned on for an instant to erase the recorded diffraction pattern on the optical space modulator 10.

Then, voltage is applied again to initialize the filter, while the test sample is moved, and the shutter is again released to permit the radiation of laser light, thereby checking whether a defect is present or not. This process is repeated until the end of the test.

Although in the above embodiment the pattern defect detecting system was applied to the detection of a defect of the integrated semiconductor circuit as the test sample, it is also applicable to other articles than such integrated semiconductor circuit, for example, a fine pattern having a mirror surface and having regularity, or a mask which is a transmission pattern.

There sometimes occurs the case where the test pattern is extremely fine and so light beams of higher order go out of the condenser lens. In this case, it is not necessary that the wave length in recording and that in testing be made the same. It is possible to select, for recording, a light source of a wave length region which is high in absorption of the optical space modulator and employ He-Ne laser or the like for the detection of defects.

According to the present invention, as set forth hereinabove, a spatial modulator capable of effecting record and erase in real-time operation is used spatially filtering diffracted light of a test sample, so the filter can be prepared in an extremely short time without requiring a development processing off-line. Besides, since it is not required to correct the tilt angle and rotational angle of a test sample, the time required for the detection can be shortened to a great extent and there is obtained a defect detecting system simpler in structure, less expensive and capable of adapting itself to a change of the test pattern.

What is claimed is:

1. A pattern defect detecting system for an integrated circuit device or the like, for detecting defects or foreign matter on a regularly arranged test pattern on a test sample by spatially filtering diffracted light from the test sample obtained by using a coherent light beam impinging on said test sample, said pattern defect detecting system having a spatial filtering means which includes an optical space element including a polarizing means and being capable of receiving and erasably recording therein a selected filter pattern including a diffraction image of said regularly arranged test pattern projected by said coherent light beam in real-time operation and erasing said selected filter pattern in real-time operation, said erasably recorded diffraction image providing a filter characteristic for the direct filtering of diffracted light from said coherent light beam.

2. A pattern defect detecting system for detecting a pattern defect of a test sample having a test pattern arranged regularly on a substrate by spatially filtering diffracted light from the test sample, said pattern defect detecting system comprising:
   (a) a coherent light source for irradiating said test sample with coherent light;
   (b) a lens for focusing a test pattern from the test sample when said test sample is irradiated with coherent light from said coherent light source;
   (c) an optical space modulator disposed at a focal point of said lens for recording diffracted light from said coherent light source of a normal pattern from the test sample in real-time in the form of a recorded filter pattern of a diffraction image of said normal pattern from said test sample projected by diffracted light from said coherent light source for intercepting and filtering the diffracted light of the normal pattern from said coherent light source, said optical space modulator including a polarizing means;
   (d) means for erasing said recorded filter pattern in said optical space modulator; and
   (e) detecting means for detecting a pattern defect of the test sample, said detecting means being disposed in an imaging position of said lens.

3. A pattern defect detecting system according to claim 1 or claim 2, wherein said optical space modulator comprises an electro-optical material having photoconductivity and Pockels effect, said polarizer means is provided on an input side of said electro-optical material, and an analyzer is provided on an output side of said electro-optical material.

4. A pattern defect detecting system according to claim 1 or claim 2, wherein both the normal pattern of said test sample and the pattern from said test sample to be filtered are formed by coherent light reflected from said test sample.

5. A pattern defect detecting system according to claim 1 or claim 2, wherein said test pattern is a transmitted image of the test sample.

6. A pattern defect detecting system according to claim 1 or claim 2, wherein a single light source is used for both recording of the diffracted light and detection of a pattern defect.

7. A pattern defect detecting system according to claim 2, wherein said erasing means is constituted by a white light source.

8. A pattern defect detecting system according to claim 2, wherein said detecting means is composed of a camera disposed in the imaging position of the lens and a signal processing portion which processes an output signal provided from said camera and detects a defective position.

* * * * *